US011730000B2

(12) United States Patent
Harari et al.

(10) Patent No.: US 11,730,000 B2
(45) Date of Patent: Aug. 15, 2023

(54) 3-DIMENSIONAL NOR STRING ARRAYS IN SEGMENTED STACKS

(71) Applicant: Sunrise Memory Corporation, San Jose, CA (US)

(72) Inventors: Eli Harari, Saratoga, CA (US); Wu-Yi Chien, San Jose, CA (US)

(73) Assignee: SunRise Memory Corporation, San Jose, CA (US)

( * ) Notice: Subject to any disclaimer, the term of this patent is extended or adjusted under 35 U.S.C. 154(b) by 17 days.

(21) Appl. No.: 17/493,502

(22) Filed: Oct. 4, 2021

(65) Prior Publication Data
US 2022/0025532 A1 Jan. 27, 2022

Related U.S. Application Data

(63) Continuation of application No. 16/859,960, filed on Apr. 27, 2020, now Pat. No. 11,180,861, which is a
(Continued)

(51) Int. Cl.
*H10B 69/00* (2023.01)
*H01L 23/528* (2006.01)
(Continued)

(52) U.S. Cl.
CPC .............. *H10B 69/00* (2023.02); *B01J 37/16* (2013.01); *C01G 3/00* (2013.01); *C07C 1/12* (2013.01);
(Continued)

(58) Field of Classification Search
CPC ............ H01L 27/115; H01L 27/11521; H01L 27/11556; H01L 23/528; H01L 27/11578;
(Continued)

(56) References Cited

U.S. PATENT DOCUMENTS

| 4,213,139 A | 7/1980 | Rao |
| 5,583,808 A | 12/1996 | Brahmbhatt |

(Continued)

FOREIGN PATENT DOCUMENTS

| JP | 2010108522 A1 | 5/2010 |
| JP | 2011028540 A1 | 2/2011 |

(Continued)

OTHER PUBLICATIONS

"EP Extended Search Report EP168690149.3", dated Oct. 18, 2019.
(Continued)

*Primary Examiner* — Thanhha S Pham
(74) *Attorney, Agent, or Firm* — Edward C. Kwok; VLP Law Group LLP

(57) ABSTRACT

A memory structure formed above a semiconductor substrate includes two or more modules each formed on top of each other separated by a layer of global interconnect conductors. Each memory module may include a 3-dimensional array of memory transistors organized as NOR array strings. Each 3-dimensional array of memory transistors is provided vertical local word lines as gate electrodes to the memory transistors. These vertical local word lines are connected by the layers of global interconnect conductors below and above the 3-dimensional array of memory transistors to circuitry formed in the semiconductor substrate.

8 Claims, 3 Drawing Sheets

Related U.S. Application Data continuation of application No. 16/006,573, filed on Jun. 12, 2018, now Pat. No. 10,692,874.

(60) Provisional application No. 62/522,661, filed on Jun. 20, 2017.

(51) Int. Cl.
| | |
|---|---|
| *H10B 41/27* | (2023.01) |
| *H10B 41/30* | (2023.01) |
| *H10B 43/00* | (2023.01) |
| *H10B 43/20* | (2023.01) |
| *H10B 43/30* | (2023.01) |
| *G11C 16/04* | (2006.01) |
| *C25B 11/051* | (2021.01) |
| *C25B 3/25* | (2021.01) |
| *C25B 11/075* | (2021.01) |
| *B01J 37/16* | (2006.01) |
| *C01G 3/00* | (2006.01) |
| *C07C 1/12* | (2006.01) |
| *C22B 15/00* | (2006.01) |
| *C30B 7/14* | (2006.01) |
| *C30B 29/02* | (2006.01) |
| *C30B 29/64* | (2006.01) |

(52) U.S. Cl.
CPC ............... *C22B 15/00* (2013.01); *C25B 3/25* (2021.01); *C25B 11/051* (2021.01); *C25B 11/075* (2021.01); *C30B 7/14* (2013.01); *C30B 29/02* (2013.01); *C30B 29/64* (2013.01); *G11C 16/04* (2013.01); *H01L 23/528* (2013.01); *H10B 41/27* (2023.02); *H10B 41/30* (2023.02); *H10B 43/00* (2023.02); *H10B 43/20* (2023.02); *H10B 43/30* (2023.02); *C07C 2523/72* (2013.01)

(58) Field of Classification Search
CPC ......... H01L 27/11568; H01L 27/11563; G11C 16/04; H10B 41/20; H10B 41/27; H10B 41/30; H10B 43/00; H10B 43/20; H10B 43/30; H10B 69/00
See application file for complete search history.

(56) References Cited

U.S. PATENT DOCUMENTS

| | | |
|---|---|---|
| 5,646,886 A | 7/1997 | Brahmbhatt |
| 5,656,842 A | 8/1997 | Iwamatsu |
| 5,768,192 A | 6/1998 | Eitan |
| 5,789,776 A | 8/1998 | Lancaster et al. |
| 5,915,167 A | 6/1999 | Leedy |
| 6,040,605 A | 3/2000 | Sano et al. |
| 6,107,133 A | 8/2000 | Furukawa et al. |
| 6,118,171 A | 9/2000 | Davies et al. |
| 6,130,838 A | 10/2000 | Kim et al. |
| 6,314,046 B1 | 11/2001 | Kamiya et al. |
| 6,362,508 B1 | 3/2002 | Rasovaky et al. |
| 6,434,053 B1 | 8/2002 | Fujiwara |
| 6,580,124 B1 | 6/2003 | Cleeves et al. |
| 6,744,094 B2 | 6/2004 | Forbes |
| 6,774,458 B2 | 8/2004 | Fricke et al. |
| 6,873,004 B1 | 3/2005 | Han et al. |
| 6,881,994 B2 | 4/2005 | Lee et al. |
| 6,946,703 B2 | 9/2005 | Ryu et al. |
| 7,005,350 B2 | 2/2006 | Walker et al. |
| 7,223,653 B2 | 5/2007 | Cheng et al. |
| 7,307,308 B2 | 12/2007 | Lee |
| 7,335,906 B2 | 2/2008 | Toda |
| 7,489,002 B2 | 2/2009 | Forbes et al. |
| 7,524,725 B2 | 4/2009 | Chung |
| 7,542,348 B1 | 6/2009 | Kim |
| 7,612,411 B2 | 11/2009 | Walker |
| 8,026,521 B1 | 9/2011 | Or-Bach et al. |
| 8,139,418 B2 | 3/2012 | Carman |
| 8,178,396 B2 | 5/2012 | Sinha et al. |
| 8,278,183 B2 | 10/2012 | Lerner |
| 8,395,942 B2 | 3/2013 | Samachisa et al. |
| 8,513,731 B2 | 8/2013 | Lee et al. |
| 8,630,114 B2 | 1/2014 | Lue |
| 8,767,473 B2 | 7/2014 | Shim et al. |
| 8,848,425 B2 | 9/2014 | Schloss |
| 8,878,278 B2 | 11/2014 | Alsmeier et al. |
| 9,190,293 B2 | 11/2015 | Wang et al. |
| 9,202,694 B2 | 12/2015 | Konevecki et al. |
| 9,230,985 B1 | 1/2016 | Wu et al. |
| 9,281,044 B2 | 3/2016 | Ramaswamy et al. |
| 9,412,752 B1 | 8/2016 | Yeh et al. |
| 9,455,268 B2 | 9/2016 | Oh et al. |
| 9,620,605 B2 | 4/2017 | Liang et al. |
| 9,633,944 B2 | 4/2017 | Kim |
| 9,748,172 B2 | 8/2017 | Takaki |
| 9,799,761 B2 | 10/2017 | Or-Bach et al. |
| 9,842,651 B2 | 12/2017 | Harari |
| 9,892,800 B2 | 2/2018 | Harari |
| 9,911,497 B1 | 3/2018 | Harari |
| 10,074,667 B1 | 9/2018 | Higashi |
| 10,096,364 B2 | 10/2018 | Harari |
| 10,121,553 B2 | 11/2018 | Harari |
| 10,157,780 B2 | 12/2018 | Wu et al. |
| 10,249,370 B2 | 4/2019 | Harari |
| 10,254,968 B1 | 4/2019 | Gazit et al. |
| 10,283,493 B1 | 5/2019 | Nishida |
| 10,373,956 B2 | 8/2019 | Gupta et al. |
| 10,381,370 B2 | 8/2019 | Shin et al. |
| 10,381,378 B1 | 8/2019 | Harari |
| 10,395,737 B2 | 8/2019 | Harari |
| 10,431,596 B2 | 10/2019 | Herner et al. |
| 10,475,812 B2 | 11/2019 | Harari |
| 10,622,377 B2 | 4/2020 | Harari et al. |
| 10,651,153 B2 | 5/2020 | Fastow et al. |
| 10,692,874 B2 | 6/2020 | Harari et al. |
| 2001/0030340 A1 | 10/2001 | Fujiwara |
| 2001/0053092 A1 | 12/2001 | Kosaka et al. |
| 2002/0012271 A1 | 1/2002 | Forbes |
| 2002/0028541 A1 | 3/2002 | Lee et al. |
| 2002/0051378 A1 | 5/2002 | Ohsawa |
| 2002/0193484 A1 | 12/2002 | Albee |
| 2003/0038318 A1 | 2/2003 | Forbes |
| 2004/0214387 A1 | 10/2004 | Madurawe et al. |
| 2004/0246807 A1 | 12/2004 | Lee |
| 2004/0262681 A1 | 12/2004 | Masuoka et al. |
| 2004/0262772 A1 | 12/2004 | Ramanathan et al. |
| 2004/0264247 A1 | 12/2004 | Kim |
| 2005/0128815 A1 | 6/2005 | Ishikawa et al. |
| 2005/0280061 A1 | 12/2005 | Lee |
| 2006/0001083 A1 | 1/2006 | Bhattacharyya |
| 2006/0155921 A1 | 7/2006 | Gorobets et al. |
| 2007/0045711 A1 | 3/2007 | Bhattacharyya |
| 2007/0134876 A1 | 6/2007 | Lai et al. |
| 2008/0178794 A1 | 7/2008 | Cho et al. |
| 2008/0239812 A1 | 10/2008 | Naofumi et al. |
| 2008/0301359 A1 | 12/2008 | Smith |
| 2009/0057722 A1 | 3/2009 | Masuoka et al. |
| 2009/0157946 A1 | 6/2009 | Arya |
| 2009/0237996 A1 | 9/2009 | Kirsch et al. |
| 2009/0279360 A1 | 11/2009 | Peter et al. |
| 2009/0290442 A1 | 11/2009 | Rajan |
| 2009/0316487 A1 | 12/2009 | Lee et al. |
| 2010/0121994 A1 | 5/2010 | Kim et al. |
| 2010/0124116 A1 | 5/2010 | Takashi et al. |
| 2010/0128509 A1 | 5/2010 | Kim et al. |
| 2010/0219392 A1 | 9/2010 | Awaya et al. |
| 2010/0254191 A1 | 10/2010 | Son et al. |
| 2011/0044113 A1 | 2/2011 | Kim |
| 2011/0115011 A1 | 5/2011 | Masuoka et al. |
| 2011/0134705 A1 | 6/2011 | Jones et al. |
| 2011/0170266 A1 | 7/2011 | Haensh et al. |
| 2011/0208905 A1 | 8/2011 | Shaeffer et al. |
| 2011/0298013 A1 | 12/2011 | Hwang et al. |
| 2011/0310683 A1 | 12/2011 | Gorobets |

(56) References Cited

U.S. PATENT DOCUMENTS

| | | |
|---|---|---|
| 2012/0182801 A1 | 7/2012 | Lue |
| 2012/0243314 A1 | 9/2012 | Takashi |
| 2012/0299079 A1* | 11/2012 | Wang ............... H01L 29/66825 |
| | | 977/773 |
| 2012/0307568 A1 | 12/2012 | Banna et al. |
| 2013/0031325 A1 | 1/2013 | Nakamoto et al. |
| 2013/0256780 A1 | 10/2013 | Kai et al. |
| 2013/0267046 A1 | 10/2013 | Or-Bach et al. |
| 2014/0015036 A1 | 1/2014 | Fursin et al. |
| 2014/0040698 A1 | 2/2014 | Loh et al. |
| 2014/0075135 A1 | 3/2014 | Choi et al. |
| 2014/0117366 A1 | 5/2014 | Saitoh |
| 2014/0151774 A1 | 6/2014 | Rhie |
| 2014/0229131 A1 | 8/2014 | Cohen et al. |
| 2014/0247674 A1 | 9/2014 | Karda et al. |
| 2014/0328128 A1 | 11/2014 | Louie et al. |
| 2014/0340952 A1 | 11/2014 | Ramaswamy et al. |
| 2015/0054507 A1 | 2/2015 | Gulaka et al. |
| 2015/0098272 A1 | 4/2015 | Kasolra et al. |
| 2015/0113214 A1 | 4/2015 | Sutardja |
| 2015/0155876 A1 | 6/2015 | Jayasena et al. |
| 2015/0194440 A1 | 7/2015 | Noh et al. |
| 2015/0249143 A1 | 9/2015 | Sano |
| 2015/0263005 A1 | 9/2015 | Zhao et al. |
| 2015/0372099 A1 | 12/2015 | Chen et al. |
| 2016/0013156 A1 | 1/2016 | Zhai et al. |
| 2016/0019951 A1 | 1/2016 | Park et al. |
| 2016/0035711 A1 | 2/2016 | Hu |
| 2016/0086970 A1 | 3/2016 | Peng |
| 2016/0225860 A1 | 8/2016 | Karda et al. |
| 2016/0300724 A1 | 10/2016 | Levy et al. |
| 2016/0314042 A1 | 10/2016 | Plants |
| 2017/0092370 A1 | 3/2017 | Harari |
| 2017/0092371 A1 | 3/2017 | Harari |
| 2017/0148517 A1 | 5/2017 | Harari |
| 2017/0148810 A1 | 5/2017 | Kai et al. |
| 2017/0213821 A1 | 7/2017 | Or-Bach et al. |
| 2017/0358594 A1 | 12/2017 | Lu et al. |
| 2018/0095127 A1 | 4/2018 | Pappu et al. |
| 2018/0108416 A1 | 4/2018 | Harari |
| 2018/0269229 A1 | 9/2018 | Or-Bach et al. |
| 2018/0331042 A1 | 11/2018 | Manusharow et al. |
| 2018/0366471 A1 | 12/2018 | Harari et al. |
| 2018/0366485 A1 | 12/2018 | Harari |
| 2018/0366489 A1 | 12/2018 | Harari et al. |
| 2019/0006009 A1 | 1/2019 | Harari |
| 2019/0019564 A1 | 1/2019 | Li et al. |
| 2019/0067327 A1 | 2/2019 | Herner et al. |
| 2019/0157296 A1 | 5/2019 | Harari et al. |
| 2019/0180821 A1 | 6/2019 | Harari |
| 2019/0206890 A1 | 7/2019 | Harari et al. |
| 2019/0214077 A1 | 7/2019 | Oh et al. |
| 2019/0238134 A1 | 8/2019 | Lee et al. |
| 2019/0244971 A1 | 8/2019 | Harari |
| 2019/0259769 A1 | 8/2019 | Karda et al. |
| 2019/0303042 A1 | 10/2019 | Kim et al. |
| 2019/0325945 A1 | 10/2019 | Linus |
| 2019/0325964 A1 | 10/2019 | Harari |
| 2019/0319044 A1 | 11/2019 | Harari |
| 2019/0348424 A1 | 11/2019 | Karda et al. |
| 2019/0355747 A1 | 11/2019 | Herner et al. |
| 2019/0370117 A1 | 12/2019 | Fruchtman et al. |
| 2020/0051990 A1 | 2/2020 | Harari et al. |
| 2020/0098738 A1 | 3/2020 | Herner et al. |
| 2020/0098779 A1 | 3/2020 | Cernea et al. |
| 2020/0176468 A1 | 6/2020 | Herner et al. |
| 2020/0258897 A1 | 8/2020 | Yan et al. |

FOREIGN PATENT DOCUMENTS

| | | |
|---|---|---|
| KR | 20120085591 A1 | 8/2012 |
| KR | 20120085603 A | 8/2012 |
| WO | 2018236937 A1 | 12/2018 |

OTHER PUBLICATIONS

"European Search Report, EP 16852238.1", dated Mar. 28, 2019.
"European Search Report, EP17844550.8", dated Aug. 12, 2020, 11 pages.
"Invitation to Pay Additional Fees (PCT/ISA/206), PCT/US2020/015710", dated Mar. 20, 2020, 2 pages.
"Notification of Reasons for Refusal, Japanese Patent Application 2018-527740", (English translation), dated Nov. 4, 2020, 8 pages.
"Partial European Search Report EP 16869049.3", dated Jul. 1, 2019, pp. 1-12.
"PCT Search Report and Written Opinion, PCT/US2018/038373", dated Sep. 10, 2018.
"PCT Search Report and Written Opinion, PCT/US2019/014319", dated Apr. 15, 2019.
"PCT Search Report and Written Opinion, PCT/US2019/052164", dated Feb. 27, 2020.
"PCT Search Report and Written Opinion, PCT/US2019/052446", dated Dec. 11, 2019.
"PCT Search Report and Written Opinion, PCT/US2020/015710", dated Jun. 9, 2020.
"PCT Search Report and Written Opinion, PCT/US2020/017494", dated Jul. 20, 2020, 13 pages.
"PCT Search Report and Written Opinion, PCT/US2020/065374", dated Mar. 15, 2021, 17 pages.
"PCT Search Report and Written Opinion, PCT/US2020/065670", dated Apr. 5, 2021, 12 pages.
"PCT Search Report and Written Opinion, PCT/US2021/016964", dated Jun. 15, 2021, 19 pages.
"PCT Search Report and Written Opinion, PCT/US2021/025722", dated Jun. 15, 2021, 10 pages.
Hou, S. Y., et al., "Wafer-Leval Integration of an Advanced Logic-Memory System Through the Second-Generation CoWoS Technology", IEEE Transactions on Electron Devices, vol. 64, No. 10, Oct. 2017, 4071-4077.
Kim, N., et al., "Multi-layered Vertical gate NANO Flash Overcoming Stacking Limit for Terabit Density Storage", Symposium on VLSI Tech. Dig. of Technical Papers, 2009, pp. 188-189.
Lue, H.T., et al., "A Highly Scalable 8-Layer 3D Vertical-gate {VG} TFT NANO Flash Using Junction-Free Buried Channel BE-SONOS Device", Symposium on VLSI: Tech. Dig. of Technical Papers, 2010, pp. 131-132.
Tanaka, T., et al., "A 768 GB 3b/cell 3D-Floaling-Gate NANO Flash Memory", Digest of Technical Papers, the 2016 IEEE International Solid-Slate Circuits Conference, 2016, pp. 142-144.
Wann, H.C., et al., "High-Endurance Ultra-Thin Tunnel Oxide in Monos Device Structure for Dynamic Memory Application", IEEE Electron Device letters, vol. 16, No. 11, Nov. 1995, pp. 491-493.

* cited by examiner

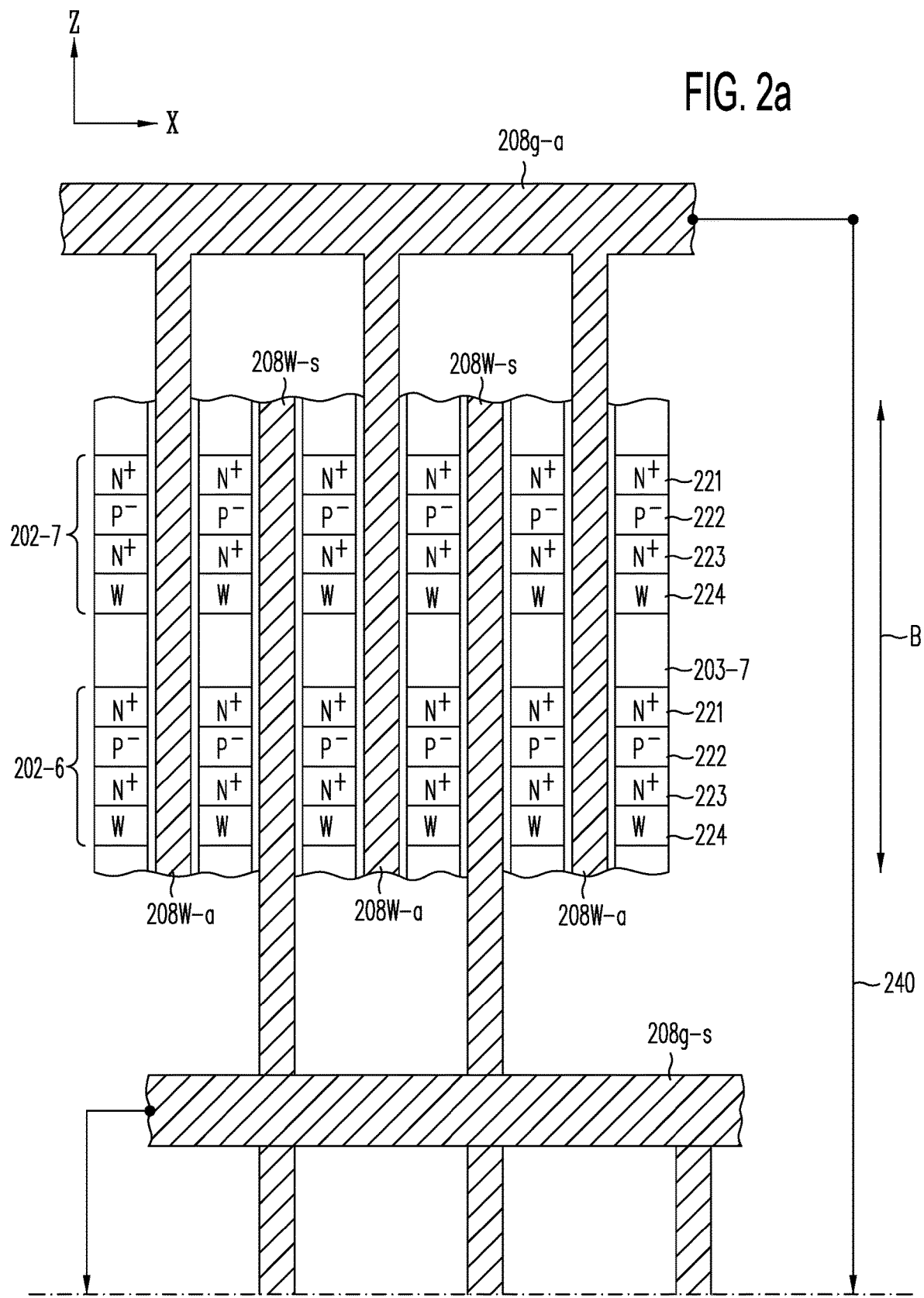

KEY TO

3-DIMENSIONAL NOR STRING ARRAYS IN SEGMENTED STACKS

CROSS REFERENCES TO RELATED APPLICATIONS

This application is a continuation application of U.S. patent application ("Parent application"), Ser. No. 16/859,960, entitled "3-Dimensional NOR String Arrays in Segmented Stacks," filed on Apr. 27, 2020, which is a continuation application of U.S. patent application Ser. No. 16/006,573, entitled "3-Dimensional NOR String Arrays in Segmented Stacks," filed on Jun. 12, 2018, which is related to and claims priority of U.S. provisional application ("Provisional application"), Ser. No. 62/552,661, entitled "3-Dimensional NOR String Arrays in Segmented. Stacks," filed on Jun. 20, 2017. This application is related to U.S. patent application ("Non-provisional application"), Ser. No. 15/248,420, entitled "Capacitive-Coupled Non-Volatile Thin-film Transistor Strings in Three-Dimensional Arrays," filed Aug. 26, 2016. The Parent Application, the Provisional application and the Non-provisional application are hereby incorporated by reference in their entireties.

BACKGROUND OF THE INVENTION

1. Field of the Invention

The present invention relates to non-volatile NOR-type memory strings. In particular, the present invention relates to manufacturing processes for forming non-volatile NOR-type memory strings in a 3-dimensional semiconductor structure.

2. Discussion of the Related Art

In the Copending Application, FIGS. 2$i$, 2$i$-1, 2$j$, 2$k$, and 2$k$-1 show three-dimensional memory structures in which the NOR strings are formed out of stacks of active strips, with each active strip being formed out of multiple layers of semiconductor material. Typically, in such a memory structure, there may be 4, 8, 16, 32 or more active layers. See, e.g., in FIG. 2$i$ of the Copending Non-provisional Application, reproduced herein as FIG. 1, two vertically stacked active layers 202-6 and 202-7, isolated from each other by isolation layer 203-7, are each provided to form multiple NOR strings. As shown in FIG. 1, each of active layers 202-6 and 202-7 includes semiconductor layers 221-223. With the large number of active layers, the resulting stack can be exceedingly tall, making it challenging to anisotropically etch narrow trenches all the way down to the bottom of the memory structure, underneath which is a semiconductor substrate at which support circuits (e.g., sense amplifiers and decoders) are often formed. Furthermore, the resulting tall and narrow stacks may be mechanically unstable, requiring supporting struts or structures. Additionally, the vertical local word-lines (e.g., word lines 208W-s and 208W-a in FIG. 1)—which are formed inside these long and narrow trenches—present high resistance R and large RC time constants which delay the response time for addressed memory strings that are furthest away from global word lines 208$g$-$a$ and 208$g$-$s$.

The tall and narrow anisotropically etched trenches may be mitigated by using a segmented stack technique, which is used in recent years in horizontal NAND strings. One example of the segmented stack technique is disclosed in the article ("Kim"), "Multi-layered Vertical Gate NAND Flash Overcoming Stacking Limit for Terabit Density Storage," by W. Kim et. al., published in the 2009 Symposium on VLSI Tech., Dig. Of technical papers, pp 188-189. However, the multi-layered NOR strings, such as those shown in the Copending Non-provisional Application, require a different interconnect scheme than the interconnect scheme of the NAND strings in the Kim article.

SUMMARY

According to one embodiment of the present invention, a memory structure formed above a semiconductor substrate includes two or more modules each formed on top of each other separated by a layer of global interconnect conductors. Each memory module may include a 3-dimensional array of memory transistors organized as NOR array strings. Each 3-dimensional array of memory transistors is provided vertical local word lines as gate electrodes to the memory transistors. These vertical local word lines are connected by the layers of global interconnect conductors below and above the 3-dimensional array of memory transistors to circuitry formed in the semiconductor substrate.

More specifically, according to one embodiment of the present invention, a memory structure includes: (a) a semiconductor substrate having a planar surface, the semiconductor substrate having circuitry formed therein and thereon; (b) memory modules provided one on top of another above the planar surface, wherein each memory module includes: (i) two or more stacks of active strips each being spaced from another along a first direction substantially parallel the planar surface, each active strip running lengthwise along a second direction that is also substantially parallel the planar surface but orthogonal to the first direction, the active strips within each stack being provided one on top of another along a third direction that is substantially perpendicular to the planar surface, each active strip being formed out of semiconductor layers that provide drain, source and channel regions of thin-film storage transistors organized as NOR strings; (ii) a set of local word line conductors each running along the third direction to provide as gate electrodes to storage transistors provided in a designated one of the stacks of active strips; (iii) a first set of global word line conductors provided below the stacks of active strips, being spaced from each other along the second direction and each running lengthwise along the first direction, connecting the substrate circuitry to some of the local word lines; and (iv) a second set of global word line conductors provided above the stacks of active strips, being spaced from each other along the second direction and each running lengthwise along the first direction, connecting the substrate circuitry to some of the local word lines, wherein the second set of global word line conductors of each memory module, except for one memory module, is provided also as the first set of global word line conductors of another memory module located immediately above it.

The present invention is better understood upon consideration of the detailed description below in conjunction with the accompanying drawings.

DETAILED DESCRIPTION OF THE PREFERRED EMBODIMENTS

Figure 1:
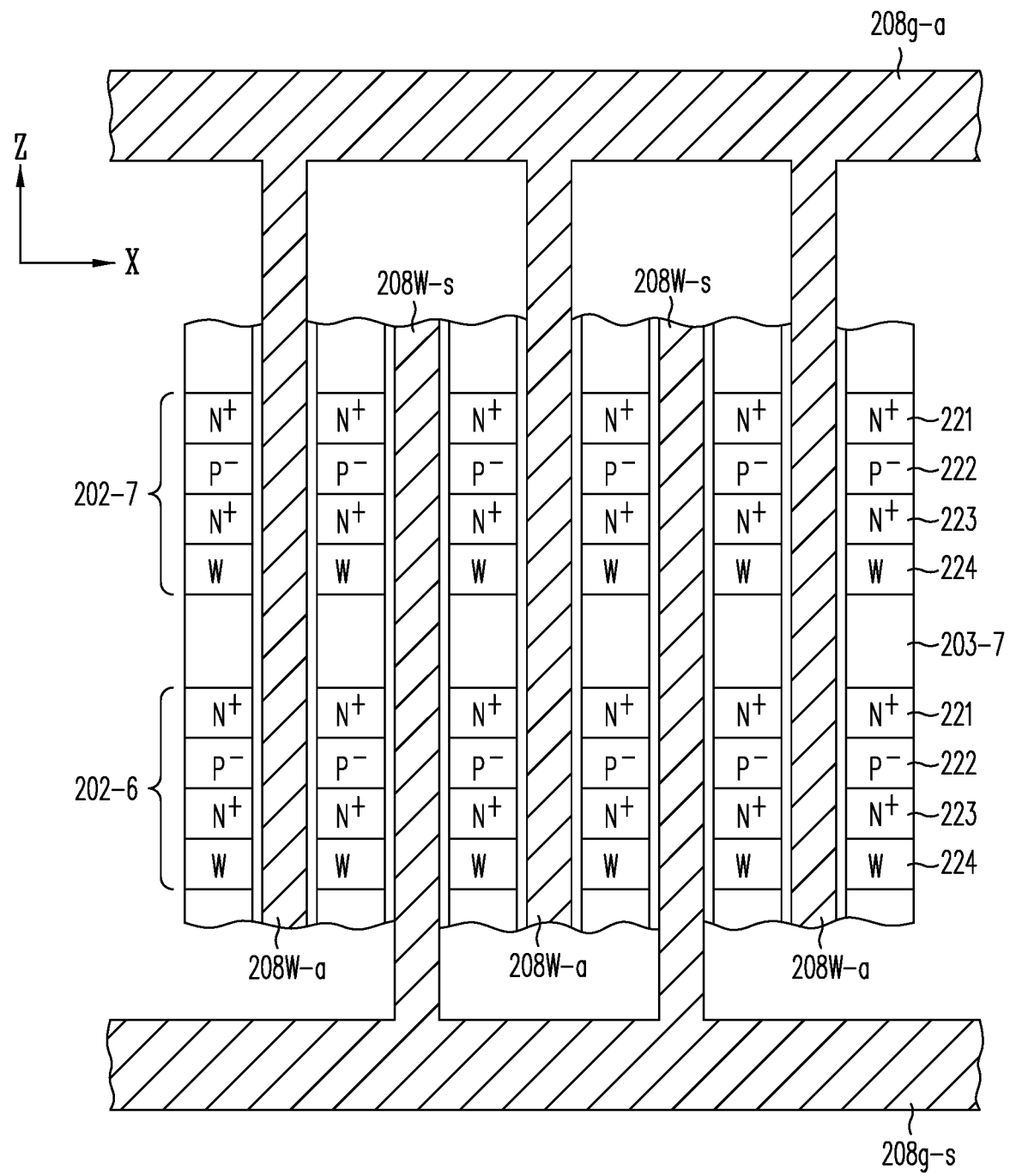
FIG. 1 reproduces FIG. 2$i$ of the Copending Non-provisional Application, showing two vertically stacked active layers 202-6 and 202-7, each provided to form multiple NOR strings out of semiconductor layers 221-223.

As shown in FIG. 1, each side edge of each active strip (e.g., active strip 202-7 or 202-6) in each active stack form a NOR string including memory transistors that are each accessed by a local word line (e.g., local word line 208W-a or 208W-s). Each local word line may be connected to circuitry in the semiconductor substrate through a global word line either from the top (e.g., global word lines 208g-a), or from the bottom (e.g., global word lines 208g-s). As shown in FIG. 1, the local word lines are shown to be connected through both top and bottom global word lines.

Figure 2B:
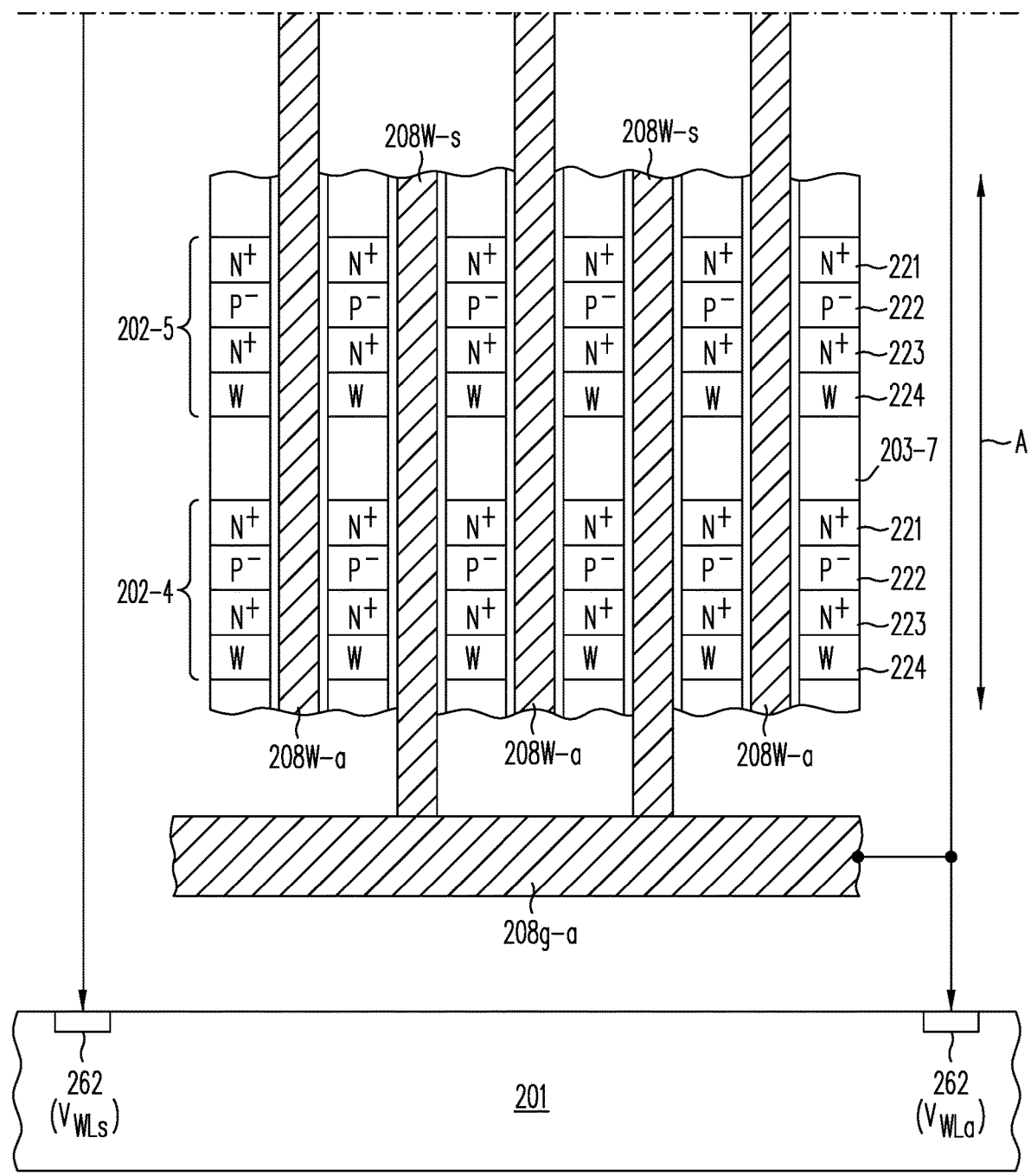
FIG. 2$a$, FIG. 2$b$, and Key to FIG. 2 shows active stacks each of at least four active strips being manufactured as two sets of half-height active stacks A and B, according to one embodiment of the present invention.
Figure 2:
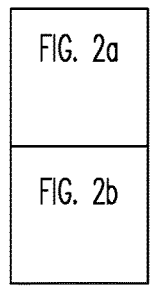

According to one embodiment of the present invention, to reduce the aspect ratio of the anisotropically etched deep trenches for local word lines 208W-a and 208W-s, and to reduce by almost half the resistance in each of these local word lines, the active stacks of the active strips in FIG. 1 may be manufactured as two or more sets of reduced-height active stacks. For example, FIG. 2 shows active stacks of at least four active strips being manufactured as two sets of half-height active stacks A and B, each active stack including two or more active strips formed therein, according to one embodiment of the present invention. In FIG. 2, half-height active stack A—which is shown to include at least active strips 202-4 and 202-5—are first formed, with local word lines 208W-a and 208W-s. Local word lines 208W-a and 208-s connect the circuitry (e.g., voltage sources $V_{WLs}$ and $V_{WLa}$) in semiconductor substrate 201 through global word lines 208g-a and global word lines 208g-s. Half-height active stacks B—which includes active strips 202-6 and 202-7—are next formed out of active layers on top of global word lines 208g-s, and share global word lines 208g-s with half-height stacks A to provide connection to the substrate circuitry. A further set of global conductors (i.e., global word lines 208g-a of half-height active strip stacks B) are next formed on top of the active layers 202-6 and 202-7 to connect the substrate circuitry to the word lines 208W-a of half-height active strip stacks B. Although this process flow involves an increased number of process steps, it substantially reduces the high aspect ratio in the etch steps and results in mechanically more sturdy structures.

The above detailed description is provided to illustrate the specific embodiments of the present invention and is not intended to be limiting. Numerous variations and modifications within the scope of the present invention are possible. The present invention is set forth by the accompanying claims.

We claim:

1. A process for forming a memory structure, comprising:
providing a semiconductor substrate having a planar surface;
forming a first memory module above the planar surface, such that the first memory module includes a 3-dimensional array of NOR-type memory strings that comprises a plurality of NOR-type memory strings, with (i) two or more of the NOR-type memory strings being separated from each other along a first direction that is substantially parallel the planar surface and two or more of the NOR-type memory strings being separated from each other along a second direction that is orthogonal to the first direction and substantially perpendicular the planar surface, (ii) each of the NOR-type memory strings comprising a plurality of thin-film storage transistors, and (iii) a set of local word line conductors, each running along the second direction to serve as gate electrodes to the thin-film storage transistors of one or more of the NOR-type memory strings;
forming a first set of global conductors, such that the global conductors are (i) spaced from each other along a third direction that is substantially orthogonal both the first and second directions and (ii) each running along the first direction, in direct contact with selected local word line conductors of the first memory module;
forming a second memory module above the first memory module and the first set of global conductors, such that the second memory module also includes a 3-dimensional array of NOR-type memory strings that comprises a plurality of NOR-type memory strings, with (i) two or more of the NOR-type memory strings being separated from each other along the first direction and two or more of the NOR-type memory strings being separated from each other along the second direction, (ii) each of the NOR-type memory strings comprising a plurality of thin-film storage transistors, and (iii) a set of local word line conductors, each running along the second direction to serve as gate electrodes to the thin-film storage transistors of one or more of the NOR-type memory strings, and such that the first set of global conductors are also each in direct contact with selected local word line conductors of the second memory module.

2. The process of claim 1, wherein the thin-film storage transistors of each NOR-type memory string within each of the first and the second memory modules share a common source region and a common drain region.

3. The process of claim 1, further comprising forming a second set of global conductors and a third set of global conductors, above the second memory module and below the first memory module, respectively, wherein, within each of the second and third sets of global conductors, the global line conductors are spaced from each other along the third direction and each running along the first direction, and wherein a first selected group of the global conductors within the second and the third set of global conductors are each in direct contact with selected local word line conductors in the second memory module and the first memory module, respectively.

4. The process of claim 3, wherein the thin-film storage transistors of each NOR-type memory string within each of the first and the second memory modules share a common source region and a common drain region, and wherein a second selected group of global conductors within the second group of global conductors are each in contact with a selected one of the common drain regions.

5. The process of claim 4, further comprising forming in and on the semiconductor substrate circuitry for supporting memory operations, the circuitry being formed such that the first set and the second set of global conductors connect the selected local word line conductors and the selected common drain regions to the circuitry.

6. The process of claim 1, further comprising forming in and on the semiconductor substrate circuitry for supporting memory operations, the circuitry being formed such that the first set of global conductors connect the selected local word line conductors to the circuitry.

7. The process of claim 6, wherein the circuitry comprises voltage sources.

8. The process of claim 6, wherein the circuitry comprises sense amplifiers.

\* \* \* \* \*